United States Patent
Park et al.

(10) Patent No.: US 10,207,963 B2
(45) Date of Patent: *Feb. 19, 2019

(54) CATALYST SYSTEM FOR OLEFIN OLIGOMERIZATION REACTION, AND METHOD FOR OLEFIN OLIGOMERIZATION USING THE SAME

(71) Applicant: LG CHEM, LTD., Seoul (KR)

(72) Inventors: Jin Young Park, Daejeon (KR); Yong Ho Lee, Daejeon (KR); Ki Soo Lee, Daejeon (KR); Eun Ji Shin, Daejeon (KR); Seok Pil Sa, Daejeon (KR); Seul Ki Im, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/549,116

(22) PCT Filed: Dec. 24, 2015

(86) PCT No.: PCT/KR2015/014279
§ 371 (c)(1),
(2) Date: Aug. 4, 2017

(87) PCT Pub. No.: WO2016/186287
PCT Pub. Date: Nov. 24, 2016

(65) Prior Publication Data
US 2018/0094085 A1    Apr. 5, 2018

(30) Foreign Application Priority Data

May 15, 2015 (KR) .................. 10-2015-0068301
Dec. 23, 2015 (KR) .................. 10-2015-0185316

(51) Int. Cl.
*C08F 4/69* (2006.01)
*C07C 11/02* (2006.01)
(Continued)

(52) U.S. Cl.
CPC ............... *C07C 2/36* (2013.01); *B01J 21/02* (2013.01); *B01J 31/14* (2013.01); *B01J 31/143* (2013.01);
(Continued)

(58) Field of Classification Search
CPC combination set(s) only.
See application file for complete search history.

(56) References Cited

U.S. PATENT DOCUMENTS

| 8,124,557 B2 | 2/2012 | Lee et al. |
| 9,988,469 B2 | 6/2018 | Song et al. |

(Continued)

FOREIGN PATENT DOCUMENTS

| CN | 103285926 A | 9/2013 |
| CN | 104511311 A | 4/2015 |

(Continued)

OTHER PUBLICATIONS

Blann, et al.: "Ethylene tetramerisation: Subtle effects exhibited by N-substituted diphosphinoamine ligands", Journal of Catalysis, Elsevier, vol. 249, 2007, pp. 244-249.

(Continued)

*Primary Examiner* — In Suk C Bullock
*Assistant Examiner* — Ali Z Fadhel
(74) *Attorney, Agent, or Firm* — Dentons US LLP

(57) ABSTRACT

Provided are a catalyst system for olefin oligomerization reaction and a method for olefin oligomerization, and more particularly, a catalyst system for olefin oligomerization reaction and a method for olefin oligomerization, which enable more efficient preparation of alpha-olefin, because a catalytic active ingredient is supported on a support, thereby exhibiting high activity in olefin oligomerization reaction even by using smaller amounts of a catalyst composition and a cocatalyst.

11 Claims, 4 Drawing Sheets

Example 1    Comparative Example 1

(51) Int. Cl.

| | | |
|---|---|---|
| C07C 2/26 | (2006.01) | |
| C08F 10/02 | (2006.01) | |
| C07C 2/36 | (2006.01) | |
| C08F 10/00 | (2006.01) | |
| C07C 2/32 | (2006.01) | |
| B01J 21/02 | (2006.01) | |
| B01J 31/14 | (2006.01) | |
| B01J 31/18 | (2006.01) | |
| B01J 31/24 | (2006.01) | |
| B01J 31/34 | (2006.01) | |
| C07C 11/04 | (2006.01) | |
| B01J 31/16 | (2006.01) | |
| B01J 31/22 | (2006.01) | |
| C08F 4/639 | (2006.01) | |
| C08F 4/6392 | (2006.01) | |
| B01J 21/08 | (2006.01) | |

(52) U.S. Cl.
CPC ....... *B01J 31/1608* (2013.01); *B01J 31/1616* (2013.01); *B01J 31/1805* (2013.01); *B01J 31/188* (2013.01); *B01J 31/2295* (2013.01); *B01J 31/24* (2013.01); *B01J 31/34* (2013.01); *C07C 2/26* (2013.01); *C07C 2/32* (2013.01); *C07C 11/02* (2013.01); *C07C 11/04* (2013.01); *C08F 4/69086* (2013.01); *C08F 10/00* (2013.01); *C08F 10/02* (2013.01); *B01J 21/08* (2013.01); *B01J 2231/122* (2013.01); *B01J 2231/20* (2013.01); *B01J 2531/46* (2013.01); *B01J 2531/48* (2013.01); *B01J 2531/62* (2013.01); *B01J 2540/10* (2013.01); *B01J 2540/52* (2013.01); *C07C 2521/08* (2013.01); *C07C 2523/26* (2013.01); *C07C 2531/14* (2013.01); *C07C 2531/18* (2013.01); *C07C 2531/22* (2013.01); *C07C 2531/24* (2013.01); *C07C 2531/34* (2013.01); *C08F 4/6392* (2013.01); *C08F 4/63916* (2013.01); *C08F 4/63925* (2013.01); *C08F 2410/03* (2013.01); *C08F 2420/02* (2013.01)

(56) References Cited

U.S. PATENT DOCUMENTS

| | | |
|---|---|---|
| 2003/0166456 A1 | 9/2003 | Wass |
| 2005/0020788 A1 | 1/2005 | Wass |
| 2005/0228139 A1 | 10/2005 | Lee et al. |
| 2006/0128910 A1 | 6/2006 | Blann et al. |
| 2006/0173226 A1 | 8/2006 | Blann et al. |
| 2006/0211903 A1 | 9/2006 | Blann et al. |
| 2006/0229480 A1* | 10/2006 | Blann .................. B01J 31/14 585/535 |
| 2008/0027188 A1* | 1/2008 | Small .................. B01J 31/143 526/113 |
| 2010/0190939 A1 | 7/2010 | Fritz et al. |
| 2011/0172370 A1 | 7/2011 | Aliyev et al. |
| 2011/0306739 A1 | 12/2011 | Carpenter et al. |
| 2012/0101321 A1 | 4/2012 | Brown et al. |
| 2012/0123078 A1 | 5/2012 | Lee et al. |
| 2012/0172645 A1 | 7/2012 | Sydora |
| 2012/0310025 A1 | 12/2012 | Wang et al. |
| 2015/0298110 A1 | 10/2015 | Cho et al. |
| 2015/0361118 A1* | 12/2015 | Lee .................. B01J 23/26 556/17 |
| 2016/0045906 A1 | 2/2016 | Sa et al. |
| 2016/0122371 A1 | 5/2016 | Lee et al. |
| 2016/0152742 A1 | 6/2016 | Lee et al. |
| 2016/0159828 A1 | 6/2016 | Lee et al. |
| 2016/0168281 A1 | 6/2016 | Lee et al. |
| 2016/0207946 A1 | 7/2016 | Shin et al. |
| 2016/0237187 A1 | 8/2016 | Hong et al. |
| 2016/0237188 A1 | 8/2016 | Hong et al. |
| 2016/0304637 A1 | 10/2016 | Lee et al. |
| 2018/0127333 A1 | 5/2018 | Lee et al. |

FOREIGN PATENT DOCUMENTS

| | | |
|---|---|---|
| EP | 2955188 A1 | 12/2015 |
| EP | 3101039 A1 | 12/2016 |
| EP | 3243848 A1 | 11/2017 |
| JP | 2006516265 A | 6/2006 |
| JP | 2011518034 A | 6/2011 |
| JP | 2012526175 A | 10/2012 |
| JP | 2013515601 A | 5/2013 |
| JP | 2018508355 A | 3/2018 |
| KR | 10-2003-0017616 A | 3/2003 |
| KR | 10-2005-0098663 A | 10/2005 |
| KR | 10-2006-0002742 A | 1/2006 |
| KR | 10-2008-0074339 A | 8/2008 |
| KR | 10-2010-0045636 A | 5/2010 |
| KR | 10-2011-0084303 A | 7/2011 |
| KR | 10-2012-0048468 A | 5/2012 |
| KR | 10-1241656 B1 | 3/2013 |
| KR | 10-2013-0142151 A | 12/2013 |
| KR | 10-2014-0063346 A | 5/2014 |
| KR | 10-2014-0126613 A | 10/2014 |
| KR | 10-2015-0037581 A | 4/2015 |
| KR | 10-2015-0057988 A | 5/2015 |
| KR | 10-2015-0058049 A | 5/2015 |
| WO | 2004/076502 A1 | 9/2004 |
| WO | 2014/175495 A1 | 10/2014 |
| WO | 2015046965 A1 | 4/2015 |
| WO | 2015072811 A1 | 5/2015 |

OTHER PUBLICATIONS

Kuhlmann, et al.: "N-substituted diphosphinoamines: Toward rational ligand design for the efficient tetramerization of ethylene", Journal of Catalysis, Elsevier, vol. 245, 2007, pp. 279-284.

Carter, et al.: "High activity ethylene trimerisation catalysts based on diphosphine ligands", Chem. Comm., 2002, pp. 858-859.

Yang, et al.: "Novel tandem catalytic system of B-diketonate zirconium/two different cocatalysts for preparing branched polyethylene", Catalysis Communications, Elsevier, vol. 10, 2009, pp. 1427-1431.

Huaiqi, et al.: "Preparation and Catalytic Performance of Silica-Supported Cr(acac)3/PNP for Ethylene Tetramerization", China Petroleum Processing and Petrochemical Technology, vol. 16, No. 1, 2014, pp. 45-51.

* cited by examiner

Example 1               Comparative Example 1

실시예 1: Example 1

비교예 1: Comparative Example 1

Comparative Example 2      Comparative Example 4

Comparative Example 2

Comparative Example 4

CATALYST SYSTEM FOR OLEFIN OLIGOMERIZATION REACTION, AND METHOD FOR OLEFIN OLIGOMERIZATION USING THE SAME

CROSS-REFERENCE TO RELATED APPLICATION

This application is a National Stage Application of International Application No. PCT/KR2015/014279, filed Dec. 24, 2015, and claims the benefit of Korean Patent Application No. 10-2015-0068301, filed May 15, 2015 and Korean Patent Application No. 10-2015-0185316, filed Dec. 23, 2015, contents of which are incorporated herein by reference in their entirety for all purposes as if fully set forth below.

TECHNICAL FIELD

The present disclosure relates to a catalyst system for olefin oligomerization reaction and a method for olefin oligomerization, and more particularly, to a catalyst system for olefin oligomerization reaction and a method for olefin oligomerization, which enable more efficient preparation of alpha-olefin, because a ligand compound is supported on a support to exhibit high activity in olefin oligomerization reaction even by using smaller amounts of a catalytic active ingredient and a cocatalyst.

BACKGROUND ART

A linear alpha-olefin is used as a cleaner, a lubricant, a plasticizer, or the like, and particularly, used as a comonomer for controlling the density of a polymer upon preparing linear low-density polyethylene (LLDPE).

In the existing preparation process of LLDPE, ethylene has been copolymerized with alpha-olefin comonomers, such as 1-hexene and 1-octene, so as to form a branch in a polymer backbone, thereby controlling the density thereof.

Thus, there is a problem in that the cost of comonomers accounts for a large part of the production cost in the preparation of LLPDE with a high comonomer content. There have been various attempts to solve the problem.

Further, since alpha-olefins have different application fields or market sizes according to the kind thereof, a technology capable of producing different olefins at the same time is commercially very important, and recently, many studies have been carried out on a chromium catalyst technology of preparing 1-hexene, 1-octene, or polyethylene with specific selectivity through ethylene oligomerization reaction or ethylene polymerization reaction.

DISCLOSURE

Technical Problem

The present invention provides a catalyst system for olefin oligomerization reaction, which exhibits high catalytic activity and selectivity for linear alpha-olefin in olefin oligomerization reaction, even though a relatively small amount of a cocatalyst is used, compared to a liquid-phase catalyst system.

Further, the present invention provides a method for olefin oligomerization using the catalyst system.

Technical Solution

The present invention provides a catalyst system for olefin oligomerization reaction, including a ligand compound including one or more diphosphine groups represented by the following Chemical Formula 1 in the molecule; a chromium source; and a support:

[Chemical Formula 1]

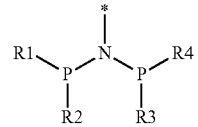

wherein P is a phosphorus atom, and N is a nitrogen atom,

R1 to R4 are the same as or different from each other, and each independently a hydrocarbyl group having 1 to 20 carbon atoms, a heterohydrocarbyl group having 1 to 20 carbon atoms, or a hydrocarboheteryl group having 1 to 20 carbon atoms, and

* represents that the group of Chemical Formula 1 is a monovalent linkage group.

In this regard, the ligand compound includes one or more the diphosphine groups represented by Chemical Formula 1, and the diphosphine groups may be linked to each other by a linker L.

The linker L may be a linker having 4 to 10 carbon atoms, which connects the diphosphine groups at the shortest distance, and the linker L may be an aliphatic linker having 2 to 20 carbon atoms, an alicyclic linker having 3 to 20 carbon atoms, or an aromatic linker having 6 to 20 carbon atoms.

According to an embodiment, all diphosphine groups may form coordinate bonds with chromium.

Specifically, a molar ratio of the chromium atoms to the ligand compound may be preferably 1 or more.

The catalyst system for olefin oligomerization reaction may include an organic chromium compound having one or more chromium complex groups represented by the following Chemical Formula 2 in the molecule:

[Chemical Formula 2]

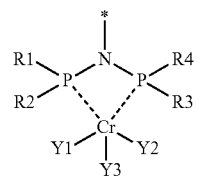

wherein P is a phosphorus atom, N is a nitrogen atom, and Cr is a chromium atom, R1 to R4 are the same as or different from each other, and each independently a hydrocarbyl group having 1 to 20 carbon atoms, a heterohydrocarbyl group having 1 to 20 carbon atoms, or a hydrocarboheteryl group having 1 to 20 carbon atoms, Y1 to Y3 are the same as or different from each other, and each independently a hydrogen atom, a halogen atom, a hydrocarbyl group having 1 to 10 carbon atoms, a heterohydrocarbyl group having 1 to 10 carbon atoms, or a hydrocarboheteryl group having 1 to 10 carbon atoms, and

* represents that the group of Chemical Formula 2 is a monovalent linkage group.

According to another embodiment of the present invention, the chromium source may be one or more compounds selected from the group consisting of chromium(III) acetylacetonate, chromium(III) chloride tetrahydrofuran, chromium(III) 2-ethylhexanoate, chromium(III) acetate, chromium (III) butyrate, chromium(III) pentanoate, chromium(III) laurate, chromium(III) tris(2,2,6,6-tetramethyl-3.5-heptanedionate), and chromium(III) stearate.

The catalyst system for olefin oligomerization reaction may further include a cocatalyst supported on the support.

In this regard, the cocatalyst may be one or more compounds selected from the group consisting of trimethyl aluminium, triethyl aluminium, triisopropyl aluminium, triisobutyl aluminum, ethylaluminum sesquichloride, diethylaluminum chloride, ethyl aluminium dichloride, methylaluminoxane, and modified methylaluminoxane.

Preferably, the cocatalyst may be supported in an amount of about 5 mmol/g to about 15 mmol/g with respect to 1 g of the support.

Meanwhile, according to another aspect of the present invention, provided is a method for olefin oligomerization, including the step of forming alpha-olefin by performing oligomerization reaction of olefinic monomers in the presence of the catalyst system.

In this regard, the olefinic monomer may be preferably ethylene.

According to an embodiment, the oligomerization reaction of olefinic monomers may be preferably performed at a temperature of about 5° C. to about 200° C. and a pressure of about 1 bar to about 300 bar.

Effect of the Invention

In a catalyst system for olefin oligomerization reaction of the present invention, catalytic metal and cocatalyst components are uniformly distributed throughout the support, and therefore, the catalyst system may exhibit high activity even though it is used in a relatively small amount.

Further, as a solid-phase supported catalyst is used, it is easy to separate the catalyst from liquid-phase reactants and products, and therefore, production of other isomers may be reduced. Further, since production of solid polyethylene occurs on the support, fouling generated on the surface of a reactor may be effectively prevented.

DETAILED DESCRIPTION OF THE EMBODIMENTS

Figure 1:
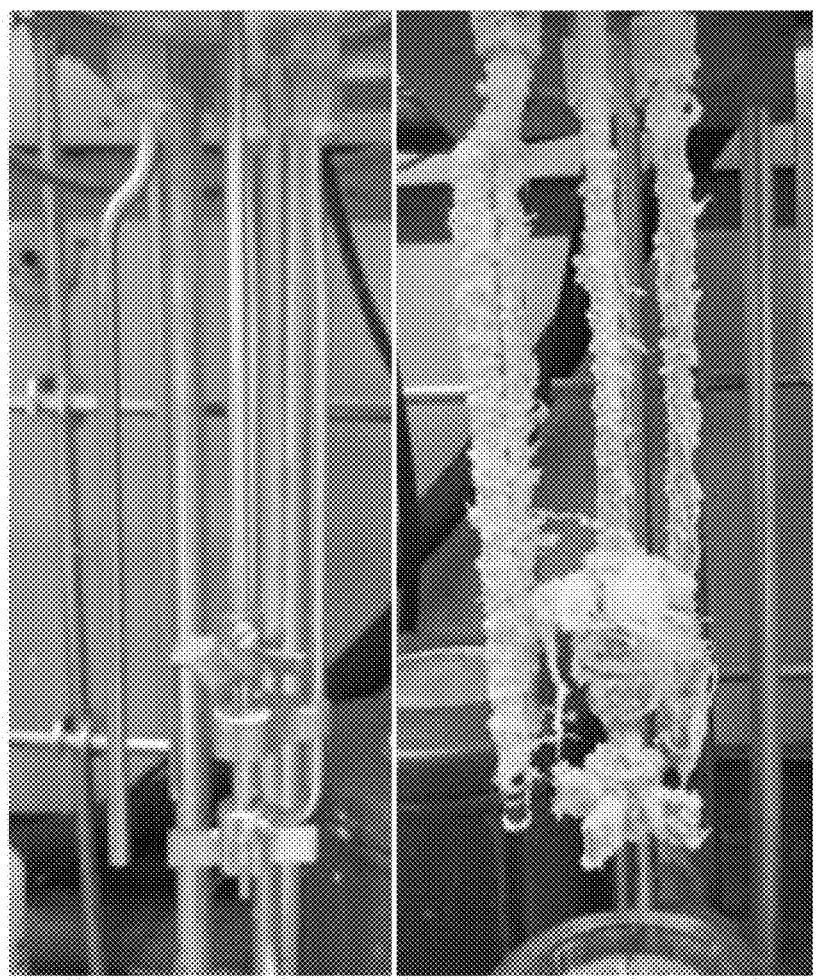
FIG. 1 shows photographs of internal devices of reactors after ethylene oligomerization reaction in Example 1 and Comparative Example 1 according to the present invention, respectively.

The terminology used herein is for the purpose of describing particular embodiments only and is not intended to be limiting of the invention. The singular forms are intended to include the plural forms as well, unless the context clearly indicates otherwise. It will be further understood that the terms "include", "have", or "possess" when used in this specification, specify the presence of stated features, integers, steps, components, or combinations thereof, but do not preclude the presence or addition of one or more other features, integers, steps, components, or combinations thereof.

While the present invention is susceptible to various modifications and alternative forms, specific embodiments thereof are shown by way of example and will herein be described in detail. It should be understood, however, that these are not intended to limit the invention to the particular form disclosed, but on the contrary, the intention is to cover all modifications, equivalents and alternatives falling within the spirit and scope of the present invention.

As used herein, the term 'oligomerization' means polymerization of a small number of olefins. For example, oligomerization collectively refers to multimerization, including trimerization or tetramerization, according to the repeating number of olefins to be polymerized. In the present invention, particularly, the oligomerization refers to selective preparation of 1-hexene and/or 1-octene, which are used as main comonomers of LLDPE, from ethylene.

As used herein, the hydrocarbyl group collectively refers to hydrocarbon compounds, for example, an alkyl group, an aryl group, an alkenyl group, an alkynyl group, a cycloalkyl group, etc., and includes both straight and branched chain forms, and both substituted and unsubstituted forms, unless otherwise specified.

As used herein, the alkylaryl group refers to an aryl group having one or more alkyl groups as substituents, and the arylalkyl group refers to an alkyl group having one or more aryl groups as substituents.

As used herein, the heteroatom refers to nitrogen, oxygen, sulfur, or phosphorus, and the heterohydrocarbyl group refers to a hydrocarbyl group having one or more heteroatoms. Such heterohydrocarbyl groups refer to those having carbon as a functionalized binding site, and the heteryl groups, such as 'hydrocarboheteryl groups', 'organoheteryl groups', etc., refer to those having a heteroatom as a functionalized binding site.

Hereinafter, the present invention will be described in more detail.

A catalyst system for olefin oligomerization reaction according to an aspect of the present invention includes a ligand compound including one or more diphosphine groups represented by the following Chemical Formula 1 in the molecule;

a chromium source; and a support:

[Chemical Formula 1]

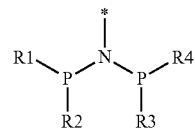

wherein P is a phosphorus atom, and N is a nitrogen atom,

R1 to R4 are the same as or different from each other, and each independently a hydrocarbyl group having 1 to 20 carbon atoms, a heterohydrocarbyl group having 1 to 20 carbon atoms, or a hydrocarboheteryl group having 1 to 20 carbon atoms, and

* represents that the group of Chemical Formula 1 is a monovalent linkage group.

The ligand compound includes diphosphino moieties in the molecule, and donates unshared electron pairs to chromium, due to abundant electron density of the nitrogen atom and the phosphorus atom.

Due to these structural features, electronic and steric characteristics of the entire ligand compound may be changed, and a bond between the ligand and the chromium atom may be changed to make the structure of the catalyst more stable, and the transition state energy, that is, the activation energy of the reaction may be changed to form alpha-olefin with higher activity and selectivity, compared to the known reaction mechanism by metallacycloheptane or metallacyclononane.

Many existing organic chromium-based catalysts may be used to prepare alpha-olefin with high activity and selectivity when a liquid-phase reaction is performed by using MAO or borate-based cocatalysts, but their reaction activity is extremely reduced when they are supported on a support, together with the cocatalyst.

However, the catalyst system according to an aspect of the present invention may be used to prepare alpha-olefin with high activity and selectivity, even when it is supported on a support such as silica, etc. In addition, since the catalyst system is at a solid phase, it is easy to separate the catalyst from liquid-phase reactants and products, and therefore, production of isomers due to adverse effects or side reactions generated when products are not separated from the catalyst may be reduced.

As such, the catalyst system may be easily separated from the reaction system, thereby reducing by-products such as solid polyethylene, etc. by side reaction of a homogeneous liquid-phase reaction.

The olefin oligomerization reaction may be performed in pores within the support, and therefore, even though solid polyethylene is formed, generation of solid polyethylene mass which is stuck inside the support upon the homogeneous liquid-phase reaction may be prevented, and problems of fouling, pipeline clogging, etc., which may be caused by the by-products remaining in the reactor, may be effectively prevented.

Furthermore, an interaction between the catalyst and the cocatalyst may easily occur because the catalytic active ingredient, chromium and the cocatalyst ingredient are supported on the same support. Accordingly, linear alpha-olefin may be polymerized with high activity, although the catalyst is used in a smaller amount than the liquid-phase catalyst.

According to an embodiment of the present invention, the ligand compound includes two or more diphosphine groups represented by Chemical Formula 1, in which the diphosphine groups are linked to each other via a linker L, for example, represented by the following Chemical Formula 1-1:

[Chmeical Formula 1-1]

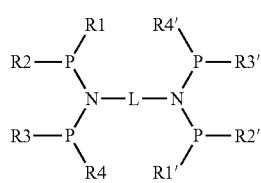

wherein P is a phosphorus atom,
N is a nitrogen atom,
R1 to R4 and R1' to R4' are the same as or different from each other, and each independently a hydrocarbyl group having 1 to 20 carbon atoms, a heterohydrocarbyl group having 1 to 20 carbon atoms, or a hydrocarboheteryl group having 1 to 20 carbon atoms, and L is a hydrocarbyl group having 2 to 30 carbon atoms or a heterohydrocarbyl group having 2 to 30 carbon atoms which connects the two or more diphosphine groups.

More specifically, in Chemical Formulae 1 and 2, R1 to R4 and R1' to R4' may be, for example, an aryl group having 6 to 20 carbon atoms, a heteroaryl group having 6 to 20 carbon atoms, or an arylheteryl group having 6 to 20 carbon atoms; or an alkylaryl group having 7 to 20 carbon atoms, a heteroalkylaryl group 7 to 20 carbon atoms, an alkylheteroaryl group 7 to 20 carbon atoms, or an alkylarylheteryl group 7 to 20 carbon atoms.

The linker (L) may be a hydrocarbyl group, a heterohydrocarbyl group, or a hydrocarbylheteryl group having various structures, and the number of atoms with the shortest distance between the diphosphine groups may be 2 to 30. Specifically, the linker may be, for example, an aliphatic linker having 2 to 20 carbon atoms, a hetero aliphatic linker having 2 to 20 carbon atoms, an alicyclic linker having 3 to 20 carbon atoms, a heteroalicyclic linker having 3 to 20 carbon atoms, an aromatic linker having 6 to 20 carbon atoms, or a heteroaromatic linker having 3 to 20 carbon atoms, but the structure is not particularly limited.

If two or more groups selected from the linkers are determined as main chains, the main chains of the linkers may have substituents of various structures.

Non-limiting examples of the above-described linker may include compounds having the following structural formulae. In the following examples, the diphosphine group represented by Chemical Formula 1 is indicated by [A], [A], or [A"] for convenience, and respective diphosphine groups may be the same as or different from each other.

(i) a plurality of diphosphine groups linked by 2 or 3 carbon atoms:

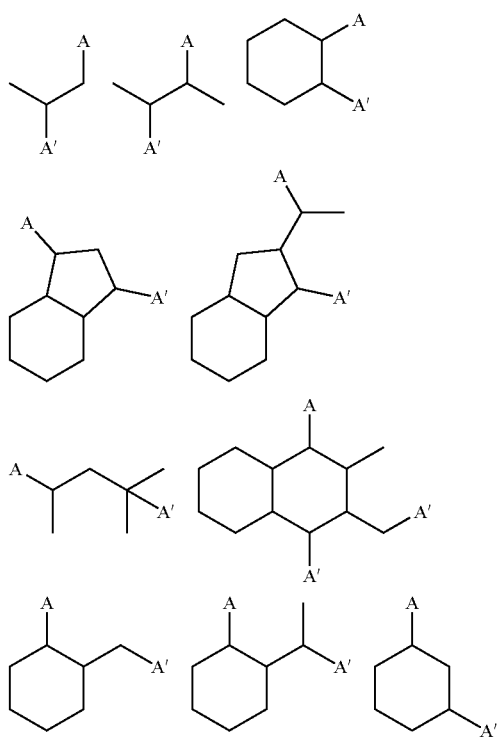

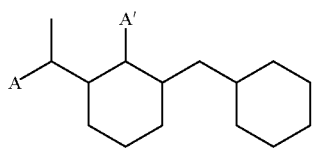

(ii) a plurality of diphosphine groups linked by 4 carbon atoms:

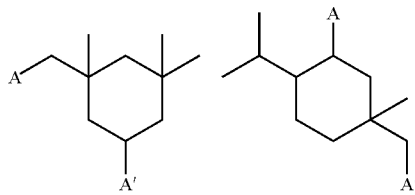

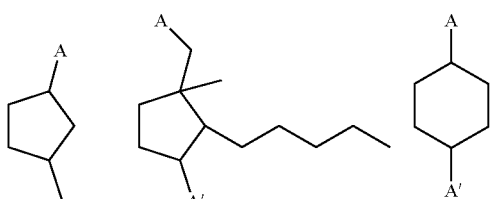

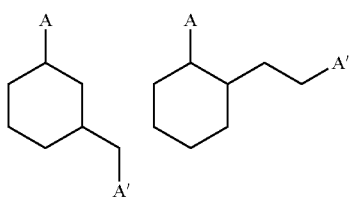

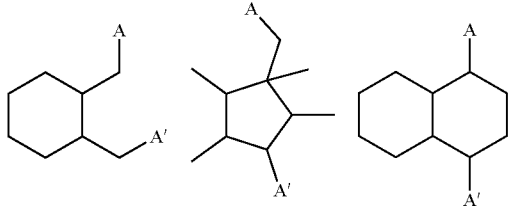

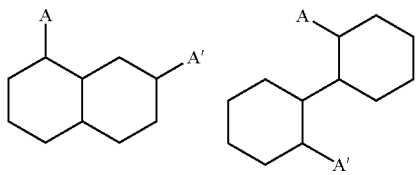

(iii) a plurality of diphosphine groups linked by 5 carbon atoms:

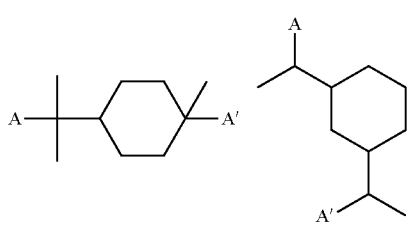

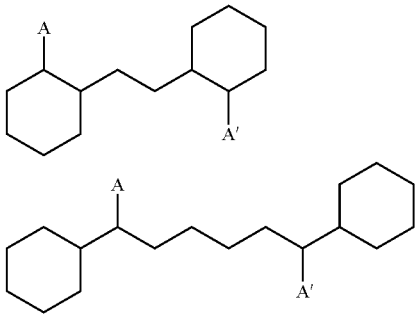

More specific examples of the linker (L) may include a first linker, a second linker, or a third linker.

In the first linker, the number of carbon atoms with the shortest distance between the diphosphine groups may be 4, and the first linker may include an aliphatic linker having 1 to 20 carbon atoms, an alicyclic linker having 3 to 20 carbon atoms, and an aromatic linker having 6 to 20 carbon atoms, and may have the following structural formulae:

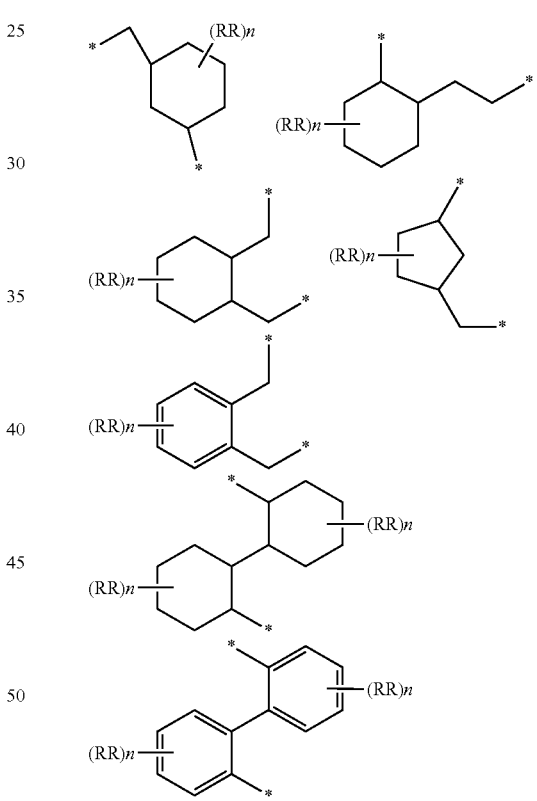

In the structural formulae, * is a region linked with the above described diphosphine group represented by Chemical Formula 1, RR are each independently an alkyl group having 1 to 5 carbon atoms, n may be the number of substitutions in each ring, and may vary within the integer range of 1 to 4 according to the number of substitutions, and a plurality of RR linked to one ring may be the same as or different from each other.

In this case, the ligand compound may have, for example, the following structural formulae:

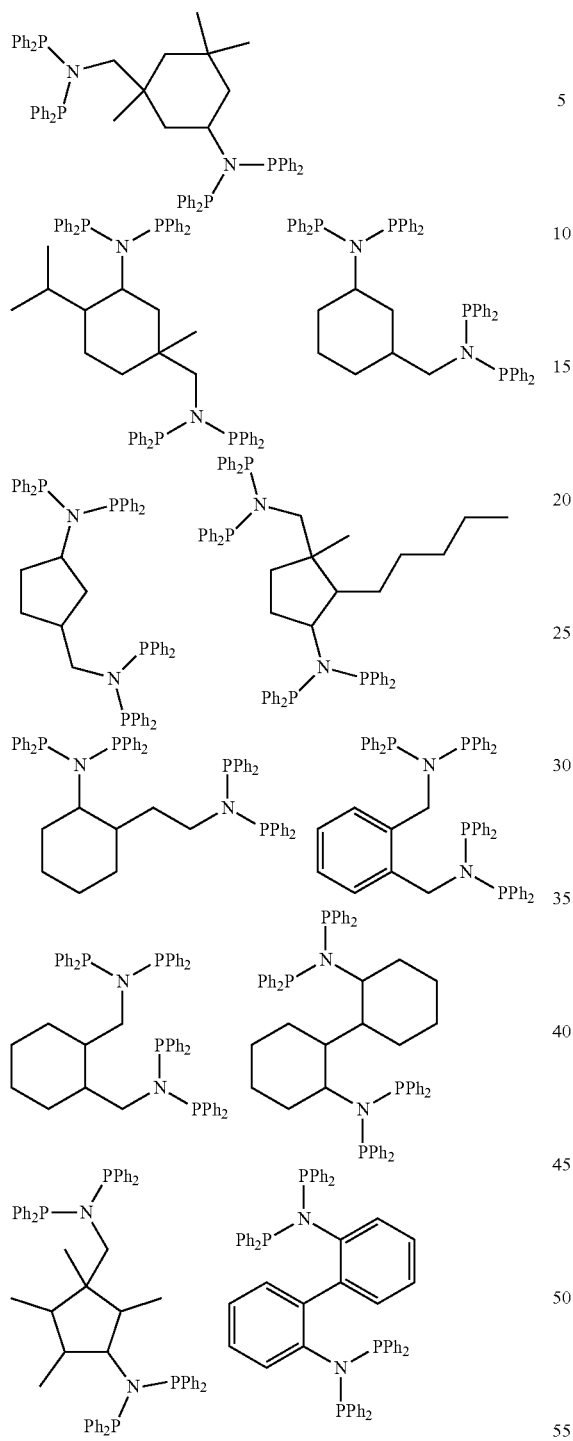

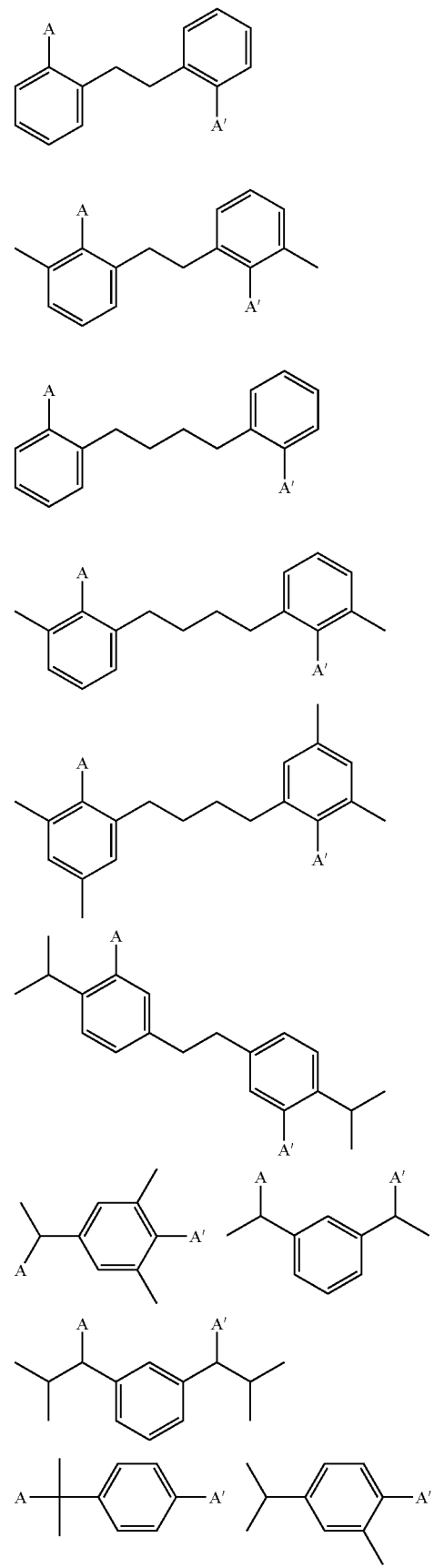

Further, in the second linker, the number of carbon atoms with the shortest distance between the diphosphine groups may be 5 to 8, and the second linker may be an aliphatic linker having 5 to 20 carbon atoms, or a linker in which an aliphatic having 1 to 20 carbon atoms and an aromatic having 6 to 20 carbon atoms are linked. Any one end of the linker may be substituted or unsubstituted with an aryl group having 6 to 20 carbon atoms.

Specifically, the second linker may have the following structural formulae:

-continued

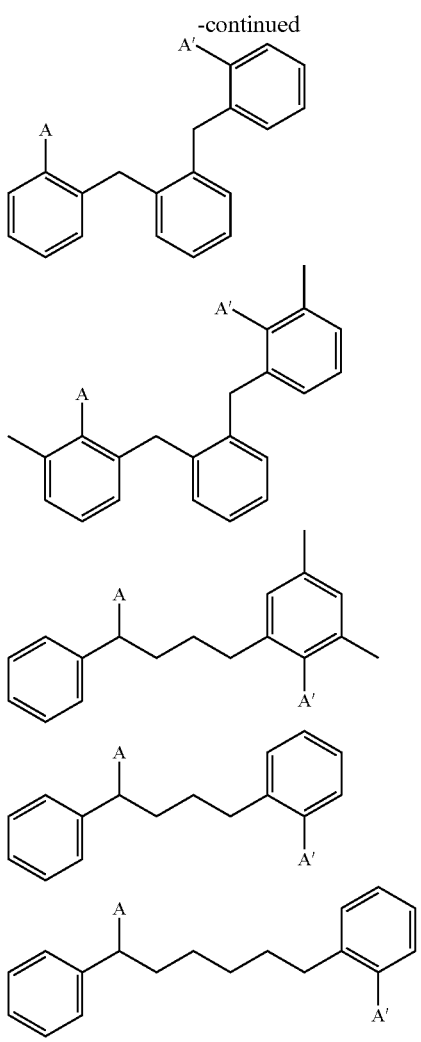

Further, in the third linker, the number of carbon atoms with the shortest distance between the diphosphine groups may be 4 to 23, and the third linker may be represented by the following Chemical Formula 3:

[Chemical Formula 3]

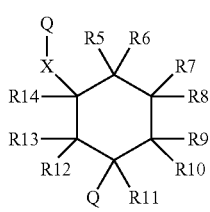

wherein Q represents the diphosphine group represented by Chemical Formula 1,

X is alkylene having 1 to 20 carbon atoms or arylene having 6 to 14 carbon atoms, R5 to R14 are the same as or different from each other, and each independently an alkyl group having 1 to 20 carbon atoms, an alkenyl group having 2 to 20 carbon atoms, an aryl group having 6 to 14 carbon atoms, an alkylaryl group having 7 to 18 carbon atoms, an arylalkyl group having 7 to 18 carbon atoms, or an alkoxyaryl group having 7 to 18 carbon atoms.

In this case, representative examples of the ligand compound may have the following structural formulae:

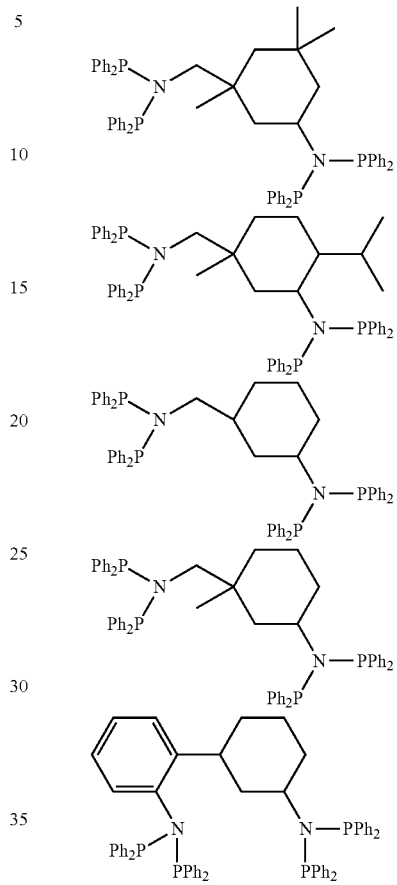

Due to the above structure of the linker (L), the activity of the supported catalyst may be further improved, and the catalyst may be advantageous in terms of selectivity for linear alpha-olefin.

According to an embodiment of the present invention, unshared electron pairs belonging to one or more diphosphine groups of the two or more diphosphine groups included in the ligand compound are coordinated to chromium atom, thereby being in the form of an organic chromium compound.

It is preferable that all the diphosphine groups form coordinate bonds with chromium, and to this end, a molar ratio of the chromium atom to the ligand compound may be 1 or more, and preferably about 1 to about 2.

For example, the catalyst system for olefin oligomerization reaction may include an organic chromium compounds having one or more chromium complex groups represented by the following Chemical Formula 2 in the molecule:

[Chemical Formula 2]

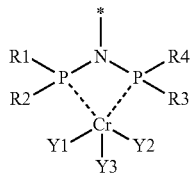

wherein P is a phosphorus atom, N is a nitrogen atom, and Cr is a chromium atom, R1 to R4 are the same as or different from each other, and each independently a hydrocarbyl group having 1 to 20 carbon atoms, a heterohydrocarbyl group having 1 to 20 carbon atoms, or a hydrocarboheteryl group having 1 to 20 carbon atoms, Y1 to Y3 are the same as or different from each other, and each independently a hydrogen atom, a halogen atom, a hydrocarbyl group having 1 to 10 carbon atoms, or heterohydrocarbyl group having 1 to 10 carbon atoms, or a hydrocarboheteryl group having 1 to 10 carbon atoms, and \* represents that the group of Chemical Formula 2 is a monovalent linkage group.

That is, the phosphorus atoms of the diphosphine group are coordinated to a chromium atom, thereby being in the form of an organic chromium compound. One molecule of the organic chromium compound may have at least one catalytic active site, preferably, two or more catalytic active sites for olefin oligomerization reaction.

Accordingly, the catalytic activity and selectivity for linear alpha-olefin may be further improved, and supporting efficiency may be improved, and detachment of the catalyst components from the support during reaction or separation may be reduced.

In this point of view, the linker (L) may more preferably include a relatively flexible aliphatic linker so that tethering of respective diphosphine groups and their functions as active sites are enhanced. For example, when the linker consists of only an alicyclic or aromatic linker without an aliphatic linker, a rigid bond greatly limits interaction, and as a result, the catalytic activity may be greatly reduced and selectivity for linear alpha-olefin may be also reduced.

Further, on the basis of the weight of the ligand compound coordinated to the chromium atom, the ligand compound may be included in an amount of about 0.5 to about 20 parts by weight, preferably about 1 to about 15 parts by weight, and more preferably about 1 to about 10 parts by weight, with respect to 100 parts by weight of the support.

According to an embodiment of the present invention, a molar ratio of the chromium atom to the ligand compound may be 1 or less, preferably, 1:1 to 10:1, and more preferably, 1:1 to 5:1.

The support has a specific surface area which is sufficient to support the catalytic components, and a general support having a large number of pores inside thereof may be used to facilitate the olefin oligomerization reaction.

That is, a metal or a non-metal, a salt or oxide thereof which is commonly used in the supported catalysts may be used as the support without particular limitation, and specific examples thereof may include silica, alumina, silica-alumina, silica-magnesia, etc., but the present invention is not limited thereto. The support may be a support dried at a high temperature, and the support may generally include a metal oxide, carbonate, sulfate, or nitrate, such as sodium oxide, potassium carbonate, barium sulfate, magnesium nitrate, etc.

It is preferable that the number of hydroxyl groups on the surface of the support is as small as possible. Practically, it is difficult to remove all of the hydroxyl groups. It is important that the number of hydroxyl groups may be controlled by adjusting drying conditions during preparation of the support. For example, the hydroxyl groups may be about 10 mmol/g or less, preferably about 1 mmol/g or less, and more preferably about 0.5 mmol/g, with respect to the weight of the support. In order to prevent side reaction due to a trace of the hydroxyl groups remaining after drying, it is possible to use a support of which hydroxyl groups are selectively removed while preserving the siloxane groups having high supporting reactivity.

In the catalyst system, a source of the chromium may be an organic or inorganic chromium compound, in which the chromium oxidation state is 0 to 6. For example, the source of the chromium may be a chromium metal or a compound in which any organic or inorganic radical binds to chromium. Herein, the organic radical may be an alkyl, alkoxy, ester, ketone, amido, or carboxylate radical having 1 to 20 carbon atoms per radical, and the inorganic radical may be halide, sulfate, oxide, etc.

Specific examples of the chromium source may be one or more compounds selected from the group consisting of chromium(III) acetylacetonate, chromium(III) chloride tetrahydrofuran, chromium(III) 2-ethylhexanoate, chromium (III) acetate, chromium(III) butyrate, chromium(III) pentanoate, chromium(III) laurate, chromium(III) tris(2,2,6,6-tetramethyl-3.5-heptanedionate), and chromium(III) stearate.

According to another embodiment of the present invention, the above-described catalyst system may further include a cocatalyst supported on the support.

Preferably, the cocatalyst may be an organic metal compound containing the Group 13 metal, and the cocatalyst is not particularly limited, as long as it may be generally used in olefin polymerization in the presence of a catalyst of a transition metal compound.

For example, the cocatalyst may be one or more compounds selected from the group consisting of compounds represented by the following Chemical Formulae 4 to 6:

—[Al(Rx)-O]$_c$—      [Chemical Formula 4]

wherein Al is aluminium,

Rx is the same as or different from each other, and each independently a halogen radical, a hydrocarbyl radical having 1 to 20 carbon atoms, a halogen-substituted hydrocarbyl radical having 1 to 20 carbon atoms, and c is an integer of 2 or more, D(Ry)$_3$      [Chemical Formula 5]

wherein D is aluminium or boron, Ry is hydrocarbyl having 1 to 20 carbon atoms or halogen-substituted hydrocarbyl having 1 to 20 carbon atoms,

[L-H]$^+$[Q(E)$_4$]$^-$      [Chemical Formula 6]

wherein L is a neutral Lewis base, [L-H]$^+$ is a Bronsted acid, Q is boron or aluminium in the +3 oxidation state, E is each independently an aryl group having 6 to 20 carbon atoms or an alkyl group having 1 to 20 carbon atoms in which one or more hydrogen atoms are substituted or unsubstituted with halogen, hydrocarbyl having 1 to 20 carbon atoms, an alkoxy functional group or a phenoxy functional group.

According to an embodiment, the compound represented by Chemical Formula 4 may include alkyl aluminoxane such as methyl aluminoxane, ethyl aluminoxane, isobutyl aluminoxane, butyl aluminoxane, etc.

According to an embodiment, the compound represented by Chemical Formula 5 may be trimethyl aluminium, triethylaluminium, triisobutylaluminium, tripropylaluminium, tributylaluminium, dimethylchloroaluminium, dimethyl-isobutylaluminium, dimethylethylaluminium, diethylchloroaluminium, triisopropylaluminium, tri-s-butylaluminium, tricyclopentylaluminium, tripentylaluminium, triisopentyl-aluminium, trihexylaluminium, ethyldimethylaluminium, methyldiethylaluminium, triphenylaluminium, tri-p-tolylaluminium, dimethylaluminiummethoxide, dimethylaluminiumethoxide, trimethylboron, triethylboron, triisobutylboron, tripropylboron, tributylboron, etc.

According to an embodiment, the compound represented by Chemical Formula 6 may be triethylammonium tetraphenylboron, tributylammonium tetraphenylboron, trimethylammonium tetraphenylboron, tripropylammonium tetraphenylboron, trimethylammonium tetra(p-tolyl)boron, tripropylammonium tetra(p-tolyl)boron, triethylammonium tetra(o,p-dimethylphenyl)boron, trimethylammonium tetra(o,p-dimethylphenyl)boron, tributylammonium tetra(p-trifluoromethylphenyl)boron, trimethylammonium tetra(p-trifluoromethylphenyl)boron, tributylammonium tetrapentafluorophenylboron, N,N-diethylanilinium tetraphenyl boron, N,N-diethylanilinium tetraphenylboron, N,N-diethylanilinium tetrapentafluorophenylboron, diethylammonium tetrapentafluorophenylboron, triphenylphosphonium tetraphenylboron, trimethylphosphonium tetraphenylboron, triethylammonium tetraphenylaluminium, tributylammonium tetraphenylaluminium, trimethylammonium tetraphenylaluminium, tripropylammonium tetraphenylaluminium, trimethylammonium tetra(p-tolyl)aluminium, tripropylammonium tetra(p-tolyl)aluminium, triethylammonium tetra(o,p-dimethylphenyl)aluminium, tributylammonium tetra(p-trifluoromethylphenyl)aluminium, trimethylammonium tetra(p-trifluoromethylphenyl)aluminium, tributylammonium tetrapentafluorophenylaluminium, N,N-diethylanilinium tetraphenylaluminium, N,N-diethylanilinium tetraphenylaluminium, N,N-diethylanilinium tetrapentafluorophenylaluminium, diethylammonium tetrapentafluorophenylaluminium, triphenylphosphonium tetraphenylaluminium, trimethylphosphonium tetraphenylaluminium, triphenylcarbonium tetraphenylboron, triphenylcarbonium tetraphenylaluminium, triphenylcarbonium tetra(p-trifluoromethylphenyl)boron, triphenylcarbonium tetrapentafluorophenylboron, etc.

Further, non-limiting examples of the cocatalyst may include an organic aluminium compound, an organic boron compound, an organic magnesium compound, an organic zinc compound, an organic lithium compound, or mixtures thereof. According to an embodiment, the cocatalyst may be preferably an organic aluminium compound, and more preferably, one or more compounds selected from the group consisting of trimethyl aluminium, triethyl aluminium, triisopropyl aluminium, triisobutyl aluminum, ethylaluminum sesquichloride, diethylaluminum chloride, ethyl aluminium dichloride, methylaluminoxane, and modified methylaluminoxane.

When both the ligand compound and the cocatalyst are supported on the support, there are no limitations in the contents of the respective components. However, a molar ratio of the ligand compound and the cocatalyst may be about 1:5 to about 1:1,000, and preferably, about 1:10 to about 1:250.

Further, the cocatalyst may be included in an amount of about 1 to about 1,000 parts by weight, preferably about 10 to about 100 parts by weight, and more preferably about 40 to about 150 parts by weight, based on 100 parts by weight of the support, respectively.

As a supported form, the ligand compound coordinated to the chromium atom and the cocatalyst may be homogeneously supported on one support or may be supported on different supports, respectively.

Further, a supporting method is not particularly limited, and the cocatalyst may be first supported, and then the ligand compound coordinated to the chromium atom may be supported. In this case, the amount of the cocatalyst to be finally supported is divided into two portions, and then supported.

Supporting of the cocatalyst and the ligand compound may be performed in the temperature range of about 20° C. to about 120° C. for about 1 hour to about 20 hours.

In detail, the supporting may include the steps of supporting the cocatalyst inside and on the surface of the support by contacting the cocatalyst with the support; and adding and supporting a mixture containing the ligand compound and the chromium source to the cocatalyst-supported support.

Further, in the step of supporting the cocatalyst, the cocatalyst feed may be divided and fed once or more times at different temperatures upon feeding the cocatalyst, and each feed temperature may be gradually decreased from the initial feed temperature, for example, at about −50° C. to about 150° C., under gradually decreasing temperature conditions.

Meanwhile, according to another aspect of the present invention, provided is a method for olefin oligomerization, including the step of forming alpha-olefin by performing oligomerization reaction of olefinic monomers in the presence of the above described catalyst system.

In this regard, the olefinic monomer may be preferably ethylene.

In general, olefin oligomerization reaction may be performed by applying a general apparatus and contact technology. For non-limiting example, a general olefin oligomerization reaction may be performed by a homogeneous liquid-phase reaction, which is conducted in the presence or absence of an inactive solvent, by a slurry reaction, in which a part of the catalyst system or all of the catalyst system is not dissolved, by a bulk-phase reaction, in which the product alpha-olefin or polyethylene acts as a main medium, or by a gas-phase reaction.

In the homogeneous liquid-phase reaction, however, production of solid polyethylene as a by-product is inevitable, and this solid polyethylene remains heterogeneously in the liquid of the reaction system, thereby reducing efficiency of the oligomerization reaction, reducing selectivity for linear alpha-olefin, and generating adverse effects such as fouling, etc.

In the present invention, however, the solid supported catalyst is used to perform the oligomerization reaction in the pores inside the supported catalyst, and therefore, the catalyst has very high stability, and morphology of oligomerization reaction may be maintained even though solid polyethylene is produced.

Further, one or more of the diphosphine groups included in the ligand compound are strongly tethered to the support, thereby reducing leaching of the catalytic active ingredients. Thus, the reaction efficiency may be increased, and the content of impurities may be reduced, as described above.

The olefin oligomerization reaction may be performed in the presence of an inert solvent. Non-limiting examples of the inert solvent may include benzene, toluene, xylene, cumene, chlorobenzene, dichlorobenzene, heptane, cyclohexane, methylcyclohexane, methylcyclopentane, n-hexane, 1-hexene, 1-octene, etc.

The olefin oligomerization reaction may be performed at a temperature of about 0° C. to about 200° C., or about 0° C. to about 150° C., or about 30° C. to about 100° C., or about 50° C. to about 100° C. Further, the reaction may be performed at a pressure of about 1 bar to about 300 bar, or 2 bar to about 150 bar.

Hereinafter, actions and effects of the present invention will be explained in further detail with reference to the specific examples of the present invention. However, these examples are merely illustrative of the present invention and the scope of the present invention is not to be determined thereby.

EXAMPLE

Preparation of Support

Silica (SP 952X, Grace Davison) was dried under vacuum at 200° C. for 12 hours to prepare a support, which was stored in a glove box under argon atmosphere.

Preparation of Catalyst System

Example 1

Preparation of

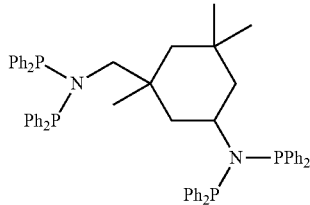

Under argon atmosphere, 5 mmol of 3-(aminomethyl)3,5,5-trimethylcyclohexaneamine and triethylamine (4 to 10 amine equivalents) were dissolved in 80 ml of dichloromethane using a flask.

While the flask was immersed in a water bath, chloroditolyphosphine (4 equivalents with respect to amine) was slowly added, and the mixture was agitated overnight.

The solvent was removed under vacuum, and then THF was added, followed by sufficient agitation, and triethylammonium chloride salt was removed using an air-free glass filter. The solvent was removed from the filtrate to obtain a ligand compound represented by the above structural formula.

In addition to this ligand compound, trivalent chromium acetate (146.7 mg, 0.42 mmol) was prepared as a chromium source, and placed in a flask at a molar ratio of chromium: ligand compound of 2:1. 65 ml of toluene was added thereto, and agitated to prepare 11 mM of an organic chromium complex.

7 g of the support thus prepared was placed in a glass reactor at 40° C., and 77 mmol of aluminium-containing methylaluminoxane (MAO) solution was added to the toluene solution, followed by supporting.

The organic chromium complex thus prepared was added thereto, and reacted by agitation for 2 hours. After stopping agitation, a filtrate was removed.

The resultant was washed with a sufficient amount of toluene, and 100 ml of hexane was added thereto, followed by agitation. A slurry solution thus prepared was transferred to an argon-purged flask, and a filtrate was removed, followed by drying under vacuum. Finally, a supported catalyst was obtained in the form of a solid powder.

Preparation Example 2

Preparation of

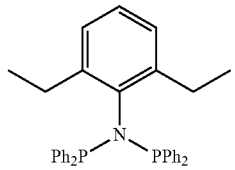

A supported catalyst was prepared in the same manner as in Preparation Example 1, except that 2,6-diethylaniline was used instead of 3-(aminomethyl)3,5,5-trimethylcyclohexaneamine, and only 0.35 mmol of chromium source was used so that a molar ratio of the ligand compound and the chromium atom was 1:1.

Preparation Example 3

Preparation of

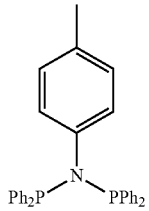

A supported catalyst was prepared in the same manner as in Preparation Example 1, except that p-toluidine was used instead of 3-(aminomethyl)3,5,5-trimethylcyclohexaneamine, and only 0.35 mmol of chromium source was used so that a molar ratio of the ligand compound and the chromium atom was 1:1.

Preparation of Ethylene Oligomer

Examples 1 to 3

Oligomerization reaction was carried out in a 600 ml-reactor made of a metal alloy, which was equipped with a mechanical stirrer, temperature-controllable, and operable at a high pressure.

30 mg of the supported catalysts prepared in Preparation Examples 1 to 3 were weighed in a dry box, and each was placed in a 50-ml glass bottle. This bottle was sealed with a rubber diaphragm, and taken out of the dry box, and prepared for injection into the reactor.

400 ml of 1.0 mmol of triethylaluminium-containing hexane and the prepared supported catalyst were fed into the reactor without contact with air, and gas-phase ethylene monomers were continuously fed at 80° C. and a pressure of 30 bar to perform oligomerization reaction for 1 hour.

Thereafter, the agitation was stopped, and unreacted ethylene was removed by degassing to terminate the reaction.

A small amount of a liquid portion in the reactor was taken and quenched with water, and an organic layer was filtered using a PTFE syringe filter, followed by GC analysis.

409 ml of ethanol/HCl (10 vol %) was added to the remaining reaction liquid, and the mixture was agitated and filtered to obtain polymers. The polymers were dried in a 60° C. vacuum oven for 12 hours or longer, followed by weighing.

Comparative Examples 1 to 3

Reaction was allowed under the same cocatalyst composition and reaction conditions as in Example 1, except that each of the organic chromium compounds prepared in Preparation Examples 1 to 3 was not supported on the support, but used as a liquid-phase catalyst to perform a homogeneous liquid-phase reaction.

The results are summarized in the following Table 1.

TABLE 1

| | Al/Cr (molar ratio) | Catalyst phase | Activity (kg/molCr/Hr) | 1-C6 (g) | 1-C8 (g) | Oligomer (g) | PE Wax (g) |
|---|---|---|---|---|---|---|---|
| Example 1 | 220 | Supported | 34028 | 12.61 | 6.82 | 19.43 | 19.41 |
| Comparative Example 1 | 220 | Liquid-phase | 5862 | 2.56 | 2.11 | 4.67 | 2.00 |
| Example 2 | 220 | Supported | 2608 | 0.58 | 0.32 | 0.91 | 3.40 |
| Comparative Example 2 | 220 | Liquid-phase | 409 | 0.05 | 0.03 | 0.08 | 0.27 |
| Example 3 | 220 | Supported | 3203 | 0.54 | 0.81 | 1.35 | 2.00 |
| Comparative Example 3 | 220 | Liquid-phase | 213 | 0.03 | 0.02 | 0.05 | 0.16 |

Referring to Table 1, although the organic chromium compound and the cocatalyst were used at the same ratio under the same conditions, the supported catalyst system showed very high catalytic activity and high selectivity for linear alpha-olefin even by using a relatively small amount of the cocatalyst.

These results seem to be attributed to the short distance between the cocatalyst and the catalytic active ingredient (ligand compound-chromium complex) which are supported on a single support, and also attributed to uniform distribution of the chromium and the cocatalyst inside and outside the support.

Further, Comparative Examples showed very low catalytic activity, compared to Examples. These results seem to be attributed to use of only 220 equivalents of the cocatalyst, although in the case of a liquid-phase catalyst system, 600 equivalents or more, preferably 900 to 1500 equivalents of the cocatalyst (based on aluminium equivalent) should be used with respect to the mole number of chromium in order to secure activity.

FIG. 1 shows photographs of internal devices of reactors after ethylene oligomerization reaction in Example 1 and Comparative Example 1 according to the present invention, respectively.

Figure 3:
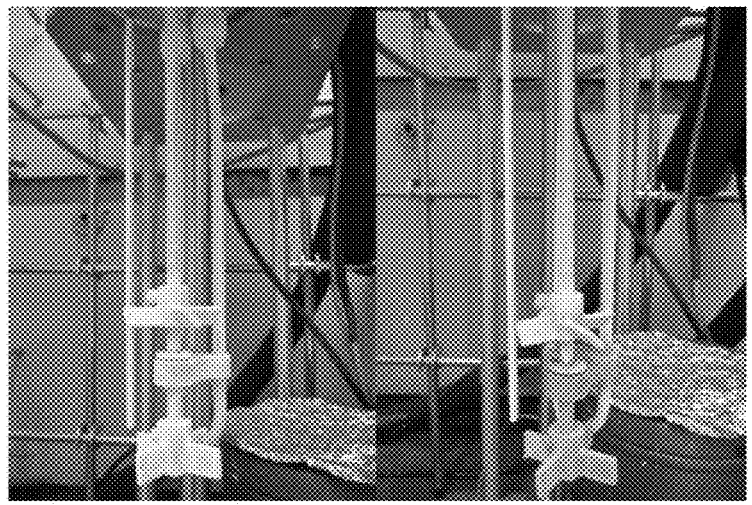
FIGS. 3 and 4 show photographs of internal devices and inner walls of reactors after ethylene oligomerization reaction in Comparative Examples 2 and 4 according to the present invention, respectively.
Figure 4:
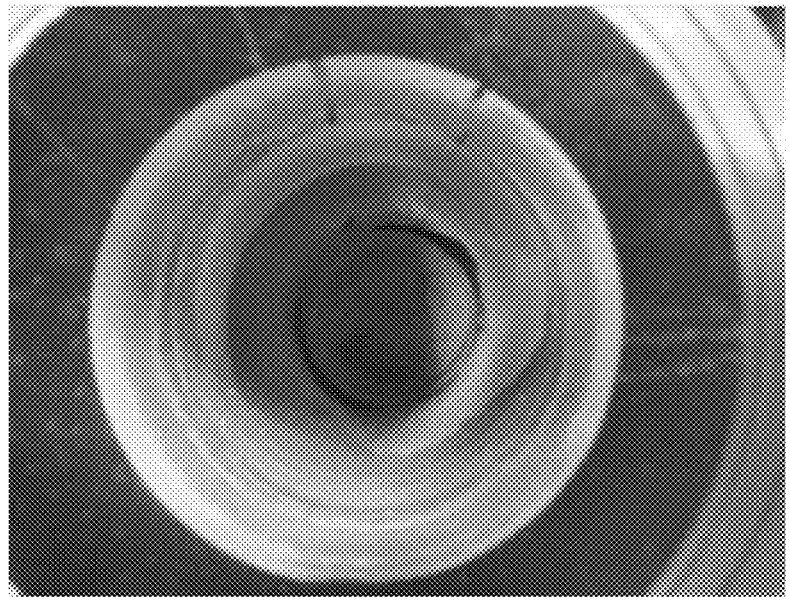
Figure 4:
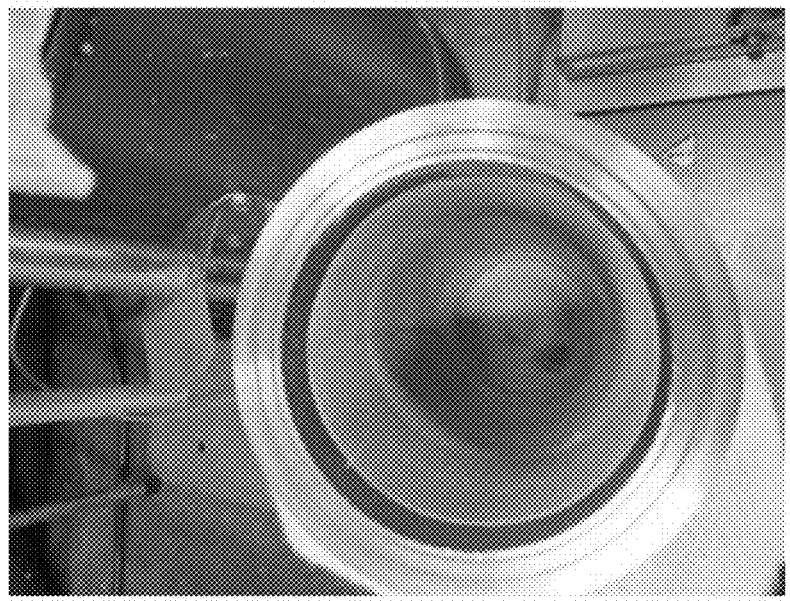

FIGS. 3 and 4 show photographs of internal devices and inner walls of reactors after ethylene oligomerization reaction in Comparative Examples 2 and 4 according to the present invention, respectively.

Referring to the above figures, in Comparative Examples, a solid product, that is, solid polyethylene stuck to the internal device and inner wall of the reactor, resulting in generation of severe fouling. In contrast, in Examples, the internal device and inner wall of the reactor were maintained clean, even after ethylene oligomerization reaction. These results seem to be attributed to high selectivity for ethylene oligomers of the supported catalyst and effective prevention of fouling, fouling being prevented because solid polyethylene exists only inside the support, although it is partially produced.

Figure 2:
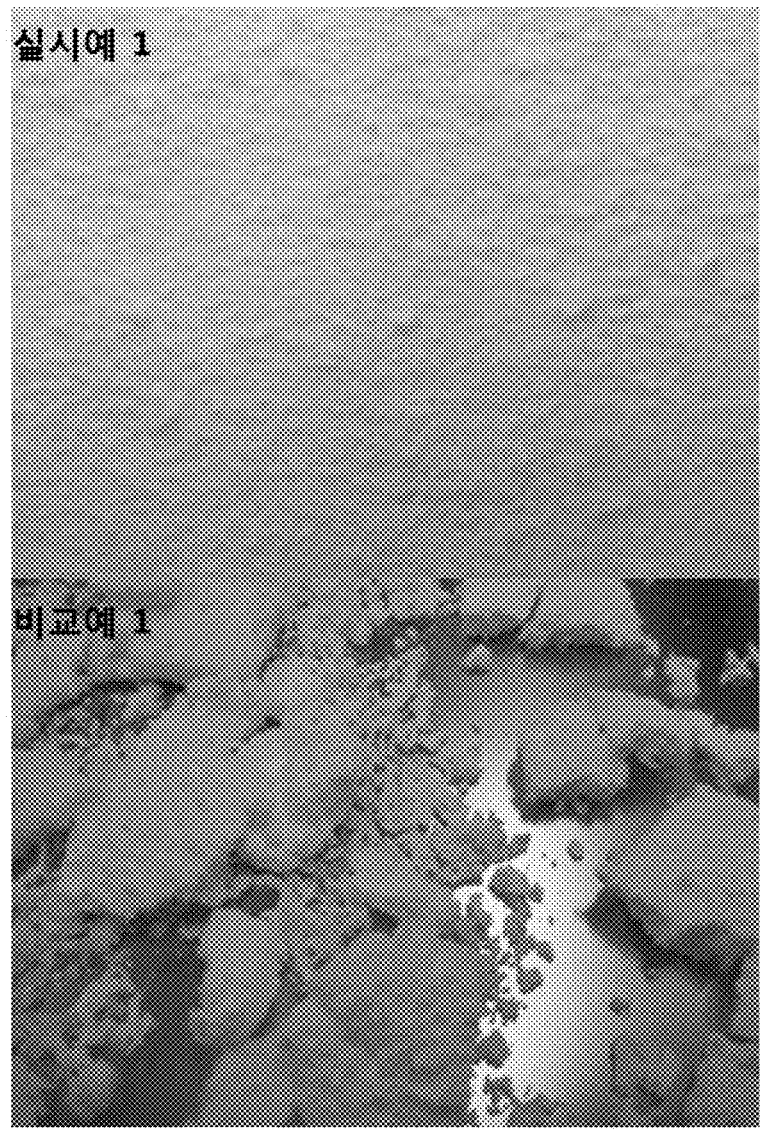
FIG. 2 shows photographs of dried solid products obtained in Example 1 and Comparative Example 1 according to the present invention, respectively.

FIG. 2 shows photographs of dried solid products obtained in Example 1 and Comparative Example 1 according to the present invention, respectively.

Referring to FIG. 2, in Comparative Example where a liquid-phase reaction was performed, morphology of the solid product was too uneven to be utilized, and aggregated particles were not broken down. In contrast, in Example, the product was obtained as a uniform powder, and therefore, availability thereof is expected to be higher than that of Comparative Example.

The invention claimed is:

1. A catalyst system for olefin oligomerization reaction, comprising:

at least one ligand compound which is selected from the following Chemical Formulas;

a chromium source; and a support:

[Chemical Formulas]

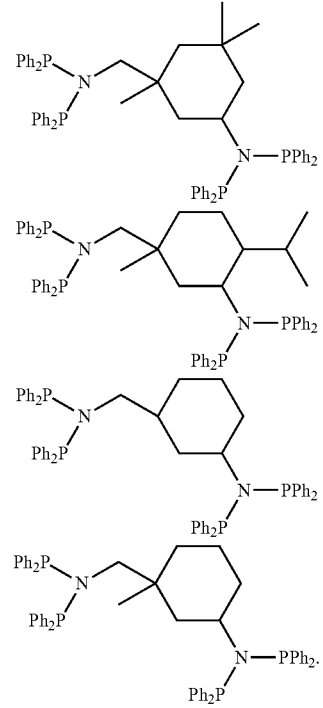

2. The catalyst system for olefin oligomerization reaction of claim 1, wherein all diphosphine groups form coordinate bonds with chromium.

3. The catalyst system for olefin oligomerization reaction of claim 1, wherein a molar ratio of the chromium source to the ligand compound is 1 or more.

4. The catalyst system for olefin oligomerization reaction of claim 1, wherein the chromium source is one or more compounds selected from the group consisting of chromium (III) acetylacetonate, chromium(III) chloride tetrahydrofuran, chromium(III) 2-ethylhexanoate, chromium(III) acetate, chromium(III) butyrate, chromium(III) pentanoate, chromium(III) laurate, chromium(III) tris(2,2,6,6-tetramethyl-3.5-heptanedionate), and chromium(III) stearate.

5. The catalyst system for olefin oligomerization reaction of claim 1, further comprising a cocatalyst supported on the support.

6. The catalyst system for olefin oligomerization reaction of claim 5, wherein the cocatalyst is one or more compounds selected from the group consisting of trimethyl aluminium, triethyl aluminium, triisopropyl aluminium, triisobutyl aluminum, ethylaluminum sesquichloride, diethylaluminum chloride, ethyl aluminium dichloride, methylaluminoxane, and modified methylaluminoxane.

7. The catalyst system for olefin oligomerization reaction of claim 5, wherein the cocatalyst is supported in an amount of 5 to 15 mmol/g with respect to 1 g of the support.

8. A method for oligomerization comprising:
oligomerizing an olefinic monomer in the presence of the catalyst system of claim 1 to form an alpha-olefin oligomer.

9. The method for oligomerization of claim 8, wherein the olefinic monomer comprises ethylene.

10. The method for oligomerization of claim 8, wherein the oligomerizing is performed at a temperature of 5° C. to 200° C.

11. The method for oligomerization of claim 8, wherein the oligomerizing is performed at a pressure of 1 bar to 300 bar.

* * * * *